US00PP19267P2

(12) United States Plant Patent
Luijten

(10) Patent No.: US PP19,267 P2
(45) Date of Patent: Sep. 23, 2008

(54) ***THUJA* PLANT NAMED '4EVER'**

(50) Latin Name: *Thuja plicata*
Varietal Denomination: 4EVER

(75) Inventor: Andreas J. M. Luijten, Steensel (NL)

(73) Assignee: Boomkwekerij Dries Luijten BV, Steensel (NL)

( * ) Notice: Subject to any disclaimer, the term of this patent is extended or adjusted under 35 U.S.C. 154(b) by 107 days.

(21) Appl. No.: 11/646,072

(22) Filed: Dec. 27, 2006

(51) Int. Cl.
*A01H 7/00* (2006.01)

(52) U.S. Cl. ..... Plt./213

(58) Field of Classification Search ..... Plt./213
See application file for complete search history.

(56) References Cited

PUBLICATIONS

UPOV ROM GITM Computer Database. GTI Jouve Retrieval Software 2007/04 Citation For '4EVER'.*

* cited by examiner

*Primary Examiner*—Wendy C. Haas

(57) ABSTRACT

A new cultivar of *Thuja* plant named '4EVER' that is characterized by an upright habit, light green leaves that turn yellow below 5 degrees Centigrade and sheds very few leaves.

1 Drawing Sheet

Botanical classification: *Thuja plicata.*
Variety denomination: '4EVER'.

BACKGROUND OF THE INVENTION

The present invention relates to a new and distinct cultivar of *Thuja* plant botanically known as *Thuja plicata* and hereinafter referred to by the cultivar name '4EVER'.

The new cultivar was discovered in 2002 in a cultivated area of Steensel, The Netherlands. '4EVER' was discovered as a single plant growing within a population of plants of *Thuja plicata* 'Martin' (not patented). The exact parents are unknown.

Asexual reproduction by softwood cuttings of the new cultivar '4EVER' first occurred in 2002 in Steensel, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Thuja* cultivar '4EVER'.

1. *Thuja* '4EVER' exhibits an upright habit.
2. *Thuja* '4EVER' exhibits light green leaves that turn yellow below 5 degrees Centigrade.
3. *Thuja* '4EVER' sheds very few leaves.

The closest comparison cultivar is *Thuja* 'Zabrina Gold' (not patented). The new cultivar '4EVER' is distinguishable from 'Zabrina Gold' by the following characteristics:

1. '4EVER' has less dense branches and foliage than 'Zabrina Gold'.
2. '4EVER' has light green leaves. The leaves of 'Zabrina Gold' are more yellow.

The new cultivar '4EVER' is distinguishable from *Thuja* 'Martin' by the following characteristics:

1. '4EVER' has light green leaves.
2. The leaves of 'Martin' do not turn yellow below 5 degrees Centigrade.

BRIEF DESCRIPTION OF THE DRAWING

The accompanying photograph illustrates the distinguishing traits of *Thuja* '4EVER'. The plant in the photograph shows an overall view of a 5 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Thuja* cultivar named '4EVER'. Data was collected in Steensel, The Netherlands from 5 year old field grown plants. The time of year was Fall. No photoperiodic treatments or growth retardants were used. Color determinations are in accordance with The Royal Horticultural Society Colour Chart 2001 edition, except where general color terms of ordinary dictionary significance are used. The growing requirements are similar to the species. '4EVER' has not been tested under all possible conditions and phenotypic differences may be observed with variations in environmental, climatic, and cultural conditions, however, without any variance in genotype.

Botanical classification: *Thuja plicata* '4EVER'.
Use: Ornamental.
Parentage: '4EVER' was discovered as a single plant growing within a population of plants of *Thuja plicata* 'Martin' (not patented). The exact parents are unknown.
Vigor: Moderate.
Growth rate: Average 22.5 cm per year.
Growth habit: Upright.
Plant shape: Conical.
Suitable container size: Field grown.
Height: Average 114 cm.
Width: Average 59.5 cm.
Hardiness: USDA Zone 6.
Propagation: Softwood cuttings.

Time to initiate roots (summer and winter): Approximately 56 days to produce roots on an initial cutting.

Root system: Fine and fibrous.

Stem:

*Branching habit.*—Main stems grow from base and have lateral branches.

*Basal branching.*—Yes.

*Average number of lateral branches.*—23.

*Pinching.*—No.

*Lateral branch diameter.*—5 mm. in diameter.

*Lateral branch length.*—32.1 cm. in length.

*Lateral branch strength.*—Moderately strong.

*Internode length.*—1.2 cm.

*Stem appearance.*—Rounded, covered with scale-like leaves, dull and smooth.

*Stem aspect.*—Rounded, covered with scale-like leaves.

*Stem strength.*—Strong.

*Stem color.*—N199B, older stems N199D.

*Pubescence.*—Absent.

Foliage:

*Texture.*—Smooth.

*Leaf arrangement.*—Opposite.

*Compound or single.*—Single.

*Leaf shape.*—Oblanceolate.

*Leaf apex.*—Acute to short apiculate.

*Leaf base.*—Cuneate.

*Leaf length.*—Average 4.8 mm in length.

*Leaf width.*—2 mm in width.

*Quantity of leaves per lateral branch.*—Average 2,000.

*Pubescence.*—Absent.

*Leaf margin.*—Entire.

*Vein pattern.*—Veins are not visible.

*Young leaf color* (*upper surface*).—15A; apexes N167A.

*Young leaf color* (*lower surface*).—15A; apexes N167A.

*Mature leaf color* (*upper surface*).—143A to 144A to 144B.

*Mature leaf color* (*lower surface*).—143B to 144A to 144B.

*Veins.*—Veins not visible.

*Leaf attachment.*—Sessile.

*Durability of foliage to stress.*—Very high.

*Fragrance.*—Western red cedar fragrance when crushed.

Flower: Flowering has not been observed.

Disease and pest resistance: '4EVER' has not been observed for disease or pest resistance.

It is claimed:

1. A new and distinct variety of *Thuja* plant named '4EVER' as described and illustrated.

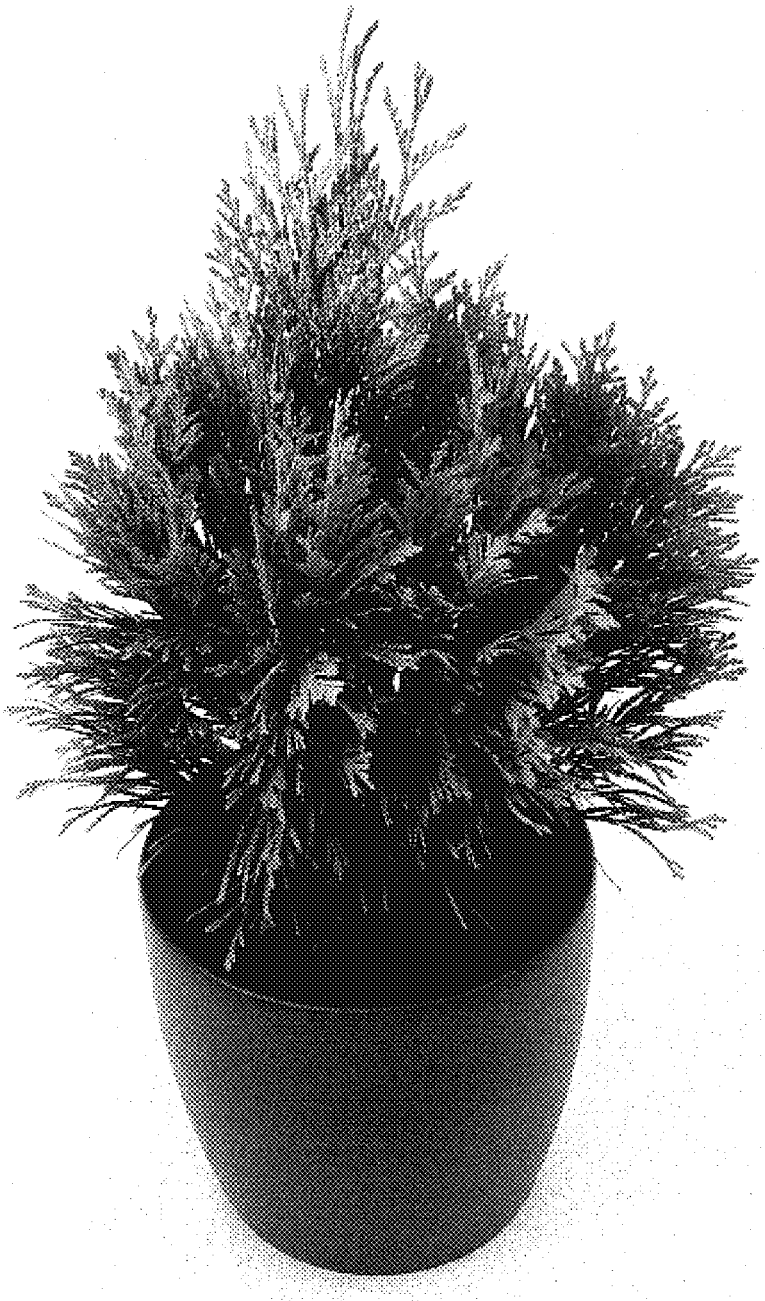

* * * * *